(12) United States Patent
Kurz et al.

(10) Patent No.: US 10,132,805 B2
(45) Date of Patent: Nov. 20, 2018

(54) MULTI-APPLICATION APPROACH FOR PHOTOMETRIC DETERMINATION OF AN ANALYTE IN A FLUID SAMPLE ON AN AUTOMATED ANALYZER

(71) Applicant: Roche Diagnostics Operations, Inc., Indianapolis, IN (US)

(72) Inventors: Georg Kurz, Penzberg (DE); Eloisa Lopez-Calle, Ludwigshafen (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 98 days.

(21) Appl. No.: 14/524,700

(22) Filed: Oct. 27, 2014

(65) Prior Publication Data

US 2015/0044780 A1 Feb. 12, 2015

Related U.S. Application Data

(63) Continuation of application No. PCT/EP2013/058674, filed on Apr. 25, 2013.

(30) Foreign Application Priority Data

| Apr. 26, 2012 | (EP) | 12002952 |
| Dec. 7, 2012 | (EP) | 12196036 |
| Dec. 21, 2012 | (EP) | 12198881 |

(51) Int. Cl.

| G01N 31/00 | (2006.01) |
| G01N 33/53 | (2006.01) |
| G01N 33/543 | (2006.01) |
| G01N 21/27 | (2006.01) |
| G01N 33/52 | (2006.01) |
| G01N 21/78 | (2006.01) |
| G01N 21/82 | (2006.01) |
| G01D 18/00 | (2006.01) |
| G01N 21/63 | (2006.01) |
| G01N 33/573 | (2006.01) |
| G01N 33/68 | (2006.01) |
| G01N 33/92 | (2006.01) |
| G06F 19/18 | (2011.01) |
| G16H 50/30 | (2018.01) |

(52) U.S. Cl.
CPC ....... G01N 33/54393 (2013.01); G01D 18/00 (2013.01); G01N 21/274 (2013.01); G01N 21/63 (2013.01); G01N 21/78 (2013.01); G01N 21/82 (2013.01); G01N 33/52 (2013.01); G01N 33/54313 (2013.01); G01N 33/54346 (2013.01); G01N 33/573 (2013.01); G01N 33/6827 (2013.01); G01N 33/92 (2013.01); G06F 19/18 (2013.01); G16H 50/30 (2018.01); G01N 2021/825 (2013.01)

(58) Field of Classification Search
None
See application file for complete search history.

(56) References Cited

U.S. PATENT DOCUMENTS

| 4,338,095 A | 7/1982 | Wu |
| 8,097,461 B2* | 1/2012 | Eck ............... C12Q 1/6876 424/520 |
| 2009/0045342 A1 | 2/2009 | Sterling et al. |
| 2011/0223066 A1 | 9/2011 | Yamazaki et al. |

FOREIGN PATENT DOCUMENTS

| EP | 0158506 B1 | 2/1990 |
| EP | 0545350 A1 | 6/1993 |
| EP | 0898169 A2 | 2/1999 |
| EP | 1460414 A1 | 9/2004 |
| EP | 1835292 A1 | 9/2007 |
| EP | 1840559 A1 | 10/2007 |
| EP | 1890142 A2 | 2/2008 |
| EP | 2645086 A2 | 10/2013 |
| JP | S63-305255 A | 12/1988 |
| JP | H07-280814 A | 10/1995 |
| WO | 1997/045728 A1 | 12/1997 |
| WO | 1999/009395 A1 | 2/1999 |
| WO | 2006/011531 A1 | 2/2006 |
| WO | 2006/104005 A1 | 10/2006 |

(Continued)

OTHER PUBLICATIONS

Vermeer et al. (Clinical Chemistry, 2005, vol. 51, pp. 244-247).*
International Search Report dated May 31, 2013, in Application No. PCT/EP2013/058674, 4 pages.
Bertsch, Thomas et al., Multicentre Analytical Evaluation of an New Point-of-Care System for the Determination of Cardiac and Thromboembolic Markers, Clinical Laboratory, 2010, pp. 37-49, vol. 56.
Armbruster, David A. and Pry, Terry, Limit of Blank, Limit of Detection and Limit of Quantitation, The Clinical Biochemist Reviews, 2008, pp. S49-S52, vol. 29, Supplement I.

(Continued)

*Primary Examiner* — Lisa V Cook
(74) *Attorney, Agent, or Firm* — Dinsmore & Shohl LLP

(57) ABSTRACT

A method for determining the amount of specific analyte of a sample which may show interferences by photometric assays, wherein the analyte is quantified from the change in the optical signal of the reaction mixture after the interaction of the analyte with analyte specific reagents. Multiple calibration curves are generated for multiple wavelengths for the specific analyte. An interference test is performed simultaneously to the determination of the specific analyte, for quantifying the amount of interfering substances present in the sample. The amount of each interfering substances is compared to predetermined cut-off values. The optical signal for the specific analyte is measured in the reaction mixture at multiple wavelengths over the complete reaction time, and a calibration curve is selected depending on the interfering substances. The amount of specific analyte is quantified by comparison with the selected calibration curve for the chosen wavelengths.

13 Claims, 3 Drawing Sheets

(56) References Cited

FOREIGN PATENT DOCUMENTS

WO     2006/132797 A2    12/2006
WO     2009/122993 A1    10/2009

OTHER PUBLICATIONS

Jhang, Jeffrey S. et al., Evaluation of Linearity in the Clinical Laboratory, Archives of Pathology & Laboratory Medicine, 2004, pp. 44-48, vol. 128.

Kelly, Alan et al., A Bichromatic Method for Total Bilirubin with a CentrifiChem 400, Clinical Chemistry, 1979, pp. 1482-1484, vol. 25, No. 8.

Li, Dong et al., Studies on selecting wavelengths during alanine aminotransferase determination, International Journal of Laboratory Medicine, 2007, pp. 602-606, vol. 28, No. 7.

Molina-Bolívar, J. A. and Galisteo-González F., Latex Immunoagglutination Assays, Journal of Macromolecular Science Part C—Polymer Reviews, 2005, pp. 59-98, vol. 45.

\* cited by examiner

MULTI-APPLICATION APPROACH FOR PHOTOMETRIC DETERMINATION OF AN ANALYTE IN A FLUID SAMPLE ON AN AUTOMATED ANALYZER

CROSS-REFERENCE TO RELATED APPLICATIONS

This application is a continuation of International Application No. PCT/EP2013/058674, filed 25 Apr. 2013, which claims the benefit of European Patent Application Nos. 12002952.5, filed 26 Apr. 2012, 12196036.3, filed 7 Dec. 2012, and 12198881.0, filed 21 Dec. 2012, the disclosures of which are hereby incorporated by reference in their entirety.

BACKGROUND

Diagnostic assays for the photometric determination of analytes in fluids, including turbidimetric, nephelometric and colorimetric assays, are common and well-known. Due to their easy one-step procedure and their short turn-around times such assays are ideal candidates for the application in automated analyzers. Today, highly automated spectrophotometric analyzers are used in the clinical diagnostics to perform photometric assays in a time- and cost-efficient manner. The workflow on the analyzer is characterized by a simple procedure without any separation or washing step, typically involving the following protocol: a) the sample (serum or plasma) containing unknown amounts of analyte and analyte-specific assay reagents are dispensed into a reaction cuvette, b) in the cuvette the sample and the reagents are allowed to incubate for a certain time period at a prescribed temperature, c) the photometer measures the optical signal of the assay solution in the cuvette which correlates with the amount of analyte in the sample.

Broad test menus based on turbidimetric, nephelometric or colorimetric assays are offered for the clinical chemistry analyzers, e.g., COBAS C (Roche Diagnostics GmbH). The detection of these assays on the COBAS C instruments is based on a photometer with a tungsten halogen lamp as irradiation source, a grating for generating monochromatic light and photodiode array (12 diodes yielding 12 wavelengths between 340 and 800 nm) as detector.

Often critical samples are submitted for routine biochemical testing at clinical laboratories which show interferences with the applied assays, thus leading to altered and wrong results.

When working with laboratory tests that use optical methods, like colorimetric and turbidimetric approaches, substances in the sample matrix that are colored or scatter the light usually cause interferences. Examples for such interfering substances are hemoglobin (hemolysis), bilirubin (icterus) and lipids (lipemia), which absorb or scatter the light at wavelengths that are commonly used for spectrophotometric tests.

Hemolysis is an important interference factor that is usually attributable to in vitro damage from erythrocytes by different factors, such as prolonged storage of the blood before separating the serum or plasma, shear forces by rapidly forcing blood through small needles, excessive agitation when mixing or the physical act of centrifugation and separation of serum. In vivo hemolysis occurs less frequently, but it has the same effect on laboratory tests. The mechanism by which hemolysis interferes with the testing procedures is the color interference by the released hemoglobin, although also leakage of analytes from damaged erythrocytes and chemical interactions between red blood cell components and analytes are also possible reasons. As consequence, falsely higher or falsely lower analyte concentrations may be obtained in clinical tests due to the hemoglobin interference. The sample can also be contaminated by constituents of other blood cells like leukocytes and platelets. For example, cell decay can result in changes in blood of patients with leukemia; the decay of platelets during coagulation results in higher concentrations of intracellular platelet constituents in serum.

Hemolysis can be further caused by biochemical, immunological, physical and chemical mechanisms. During blood transfusion, complement-dependent hemolysis may be caused by antibodies reacting with the major blood group antigens. Physical hemolysis is caused by destruction of erythrocytes by hypotonicity, e.g., dilution of blood with hypotonic solution, as well as decreased (vacuum) or increased pressure. Mechanical hemolysis can occur during the flow of blood through medical devices, e.g., catheters, heart valves in-vivo, and by inadequate centrifugation as well as elevated temperature in-vitro. Contaminating substances can also cause in-vitro hemolysis. Finally, detergents and other contaminating substances can cause hemolysis. After the separation of blood cells, hemolysis is detected by the red color of serum or plasma. At extracellular hemoglobin concentrations exceeding 300 mg/L (18.8 mmol/L), hemolysis is detectable by the red color of serum or plasma. Samples with therapeutic hemoglobin derivatives are always intensely red colored. Some analytical systems measure the extent of hemolysis by comparing the absorption of samples at two wavelengths. The absorption spectrum of the hemoglobin derived oxygen carriers used as blood substitutes does not differ substantially from that of natural hemoglobin.

Bilirubin is a yellow pigment produced by enzymatic degradation of hemoglobin. Studies on bilirubin interference were mostly based on experiments in which free bilirubin or water-soluble di-taurobilirubin was added to serum. Under certain conditions the bilirubin molecules differ qualitatively and quantitatively in their effects of interference. Conjugated bilirubin appears in urine, when present at increased concentrations in blood. In patients with proteinuria, bilirubin bound to albumin can also appear in urine. After intra-cerebral bleedings unconjugated (free) bilirubin causes xanthochromia of the cerebrospinal fluid. At increased permeability of the blood-brain barrier bilirubin bound to albumin can appear in the CSF. Bilirubin has a high absorbance between 340 nm and 500 nm wavelengths. Therefore spectrophotometric tests using these wavelengths show limitations because of the constantly high background absorbance caused by bilirubin. The apparent increase or decrease of a result by bilirubin interference is assay- and analyte concentration-dependent.

Lipemic samples are samples of blood, serum, or plasma that have a cloudy or milky appearance due to increased lipid content. Lipemic samples cannot be avoided as increased concentration of lipids is often secondary to other disease states such as: diabetes mellitus, ethanol use, chronic renal failure and pancreatitis. The presence of lipemia can interfere with many clinical chemistry tests by different mechanisms, the most frequent mechanism being the scattering of light by the lipids, mainly chylomicrons and very low density lipoproteins, VLDL. As consequence the determined analyte concentrations can be altered, depending on the applied wavelengths and the lipid content.

In conclusion, the presence of hemoglobin, bilirubin and lipids and other interfering substances in a sample can cause a positive or a negative interference in the measurement result of photometric assays aimed at the quantitation of a specific analyte. Depending on the magnitude of the interference, the results may lead to wrong interpretation and inappropriate intervention.

To overcome the drawbacks of the interferences caused by hemolysis, icterus and lipemia several methods are known in the literature. Lipemic, icteric and hemolytic interferences can be reduced by pretreatment of the sample in a pre-analytical process to remove the interfering substance, e.g., by high speed centrifugation in case of lipemic samples. However, such countermeasures increase the workload and reduce the cost- and time-efficiency; such countermeasures are also prone to errors in the sample handling.

Another strategy is to use other clinical tests which are not sensitive to interferences. This may be challenging since alternative tests may need another instrument platform not available in the laboratory; also there might be no alternative test available on the market.

A correction of interferences caused by lipemia, hemolysis and icterus by using a blanking procedure is an alternative to overcome the limitations. This involves the measurement of the sample absorbance, once suitably diluted, prior to adding the assay reagents. The absorbance measured is subtracted from the final absorbance. A strategy to realize this blanking procedure is the utilization of 2 different reagents (blank and assay reagents) and 2 cuvettes. This approach improves the results, but it suffers from one drawback, reducing the throughput of tests by half. Another method involves the sequential adding of the reagents into the cuvette: a first reading is taken after a set time; afterwards assay reagents are added and incubated; finally a second reading is made. However, only poor improvement is usually achieved with this procedure. Furthermore, the established assay protocols may not be compatible with the new initial dilution step of the sample required for the first reading.

Bichromatic analysis allows also correcting the analytical results and is often applied in automated laboratory tests. A secondary (side) wavelength is used to measure the interfering substance. The analyte to be determined does not absorb at this second wavelength. This measurement is then subtracted from that of the analyte. This assumes that the absorbance of the interfering substance is the same at both wavelengths, which rarely is the case. Therefore, the bichromatic principle will only yield slight improvements in reducing interferences. Additionally, it is possible to treat the interference by chemically eliminating the interfering substance, e.g., bilirubin with bilirubin oxidase, or vitamin C with ascorbic oxidase.

Furthermore, multi-channel analyzers are fully automated, computer-controlled systems designed for the analysis of routine chemistry assays, immunoassays, and therapeutic drugs, e.g., COBAS 6000 (Roche Diagnostics GmbH) uses spectrophotometry to perform kinetic, endpoint and non-linear reactions. To a certain extent, the system, similar to most modern analyzers, reduces spectral interference effects by application of two-reagent procedures and bichromatic spectrophotometry. The quality of the sample can be determined by different methods. A common method is to run a serum index test on the lab analyzer which quantifies the amount of bilirubin, haemoglobin and lipids present in the sample. The implementation of HIL indicies improved the accuracy and the quality of the test results.

However, there are still many patient samples showing interferences by hemolysis, bilirubin and lipids leading to erroneous results even by using HLI-indicies or correction methods. Analytical interference by hemolysis, bilirubin and lipids with laboratory assays is the most common concern in laboratory medicine. These altered and wrong results may lead to incorrect interpretation, wrong diagnosis, and potentially inappropriate intervention and unfavorable outcome for the patients. As consequence many samples have to be pretreated in a pre-analytical step to remove the interfering substance and then re-measured in cases where the concentration of hemoglobin, bilirubin, and lipids exceed a specific cut-off level. Pretreatments and re-measurements cause additional expenses and loss of time, both factors being critical for laboratories performing those assays.

SUMMARY

It is against the above background that the embodiments of the present disclosure provide certain unobvious advantages and advancements over the prior art. In particular, the inventors have recognized a need for improvements in a multi-application approach for photometric determination of an analyte in a fluid sample on an automated analyzer.

Although the embodiments of the present disclosure are not limited to specific advantages or functionality, it is noted that the present disclosure provides an improved assay method for the determination of a specific analyte in critical samples showing interferences by using the commercially available spectrophotometric laboratory tests on the corresponding instrument platform without the need to apply pre-analytical sample treatment or changing the assay methodology.

It has surprisingly been found by the inventors that an improved accuracy of a sample showing interferences is realized by the methods of the present disclosure. The present invention is expected to (at least partially) overcome the problem of pre-analytical sample treatment and remeasurements of samples showing interferences, to determine the correct amount of an specific analyte in a sample in photometric assays.

In accordance with one embodiment of the present disclosure, a method for determining the amount of the specific analyte of a sample which may show interferences by photometric assays is provided, wherein the specific analyte is quantified from the change in the optical signal of the reaction mixture after the interaction of the analyte with analyte specific assay reagents. Multiple calibration curves are generated for multiple wavelengths for the specific analyte of a sample to be determined, the measurement results are deposited in a data management system of the instrument platform. An interference test is performed simultaneously to the determination of the specific analyte, for quantifying the amount of interfering substances present in the sample to be determined. The amount of each interfering substances is compared to predetermined cut-off values. The optical signal for the specific analyte of a sample to be determined is measured in the reaction mixture at multiple wavelengths over the complete reaction time, and a calibration curve is selected depending on the interfering substances. Finally, the amount of the specific analyte of a sample to be determined is quantified by comparison with the selected calibration curve for the chosen wavelengths.

In accordance with another embodiment of the present disclosure, a method for reducing interferences of spectrophotometric-based laboratory tests of samples showing hemolytic and/or icteric and/or lipemic and/or other interferences is provided, wherein specific measurement conditions comprising wavelengths for measurement, reaction times, calibration points, calibration mode are additional applied to the measurement protocol without applying pre-analytical sample treatment and/or changing the assay methodology.

In accordance with yet another embodiment of the present disclosure, use of specific measurement conditions additionally applied to the measurement protocol are provided for reducing interferences of spectrophotometric-based laboratory tests for determining the amount of a specific analyte in a sample showing interferences comprising wavelengths for measurement, reaction times, calibration points, calibration mode.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

DETAILED DESCRIPTION

Figure 1:
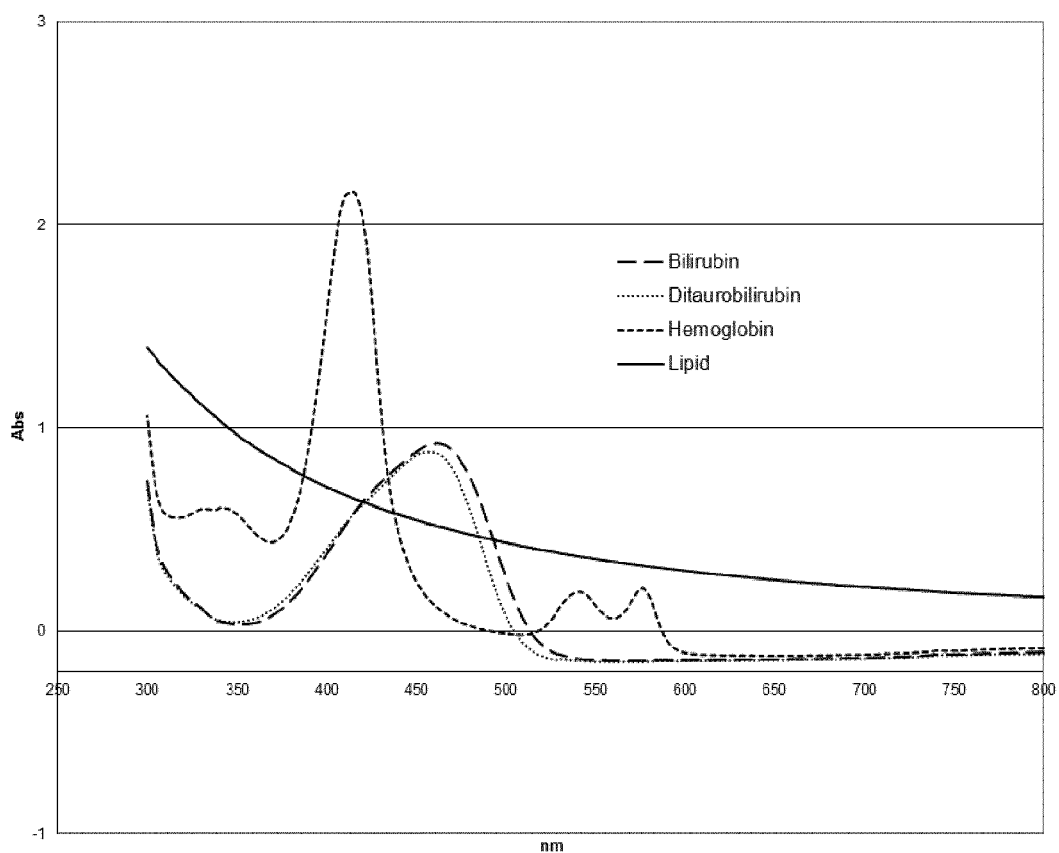
FIG. 1 shows absorption spectra of the interfering substances bilirubin, hemoglobin and lipids.

The present invention is directed to a method for determining the amount of the specific analyte of a sample that may show interferences by photometric assays, wherein the specific analyte is quantified from the change in the optical signal of the reaction mixture after the interaction of the analyte with analyte specific assay reagents on a lab analyzer. Multiple calibration curves for multiple wavelengths are generated for the specific analyte of a sample to be determined, the measurement results are deposited in a data management system of the instrument platform.

Optionally, an interference test is performed for quantifying the amount of bilirubin and/or haemoglobin and/or lipids and/or other interfering substances present in a sample to be determined, and the amount of each interfering substances is compared to predetermined cut-off values. Simultaneously, the optical signal for the specific analyte of a sample to be determined is measured in the reaction mixture at multiple wavelengths over the complete reaction time. A calibration curve is selected depending on the amount and type of interfering substances present in the sample. Finally, the amount of the specific analyte of a sample to be determined is quantified by comparison with the selected calibration curve for the chosen wavelength(s).

The method of the present disclosure further provides specific measurement conditions comprising reaction times, calibration points, calibration mode and the assay type that are additionally applied to the measurement protocol.

The quality of the sample can be determined by different methods. A common method is to run a serum index test on the lab analyzer that quantifies the amount of bilirubin, haemoglobin and lipids present in the sample. Thereby, the serum index and the measurement of the optical signal of a specific analyte can be performed simultaneously on the analyzer. Sometimes, in case of high concentrations of interfering substances, it is even possible to classify serum samples visually by their color.

By generating multiple calibration curves under multiple conditions characterized by wavelengths for measurement, reaction times, calibration mode, number of calibration points, which were predetermined for specific analyte applications, it is now possible to measure a specific analyte of theses samples more accurately in comparison with standard techniques. One or more calibration curves are selected that are optimized for reducing the interferences, leading to an expansion of the tolerated amount of interfering substances.

By using the method of the present disclosure, critical samples showing interferences, e.g., hemolytic, icteric and/or lipemic samples can now be measured using the commercially available spectrophotometric laboratory tests on the corresponding instrument platform. It has surprisingly been found by the inventors that an improved accuracy of a sample showing interferences is realized by the methods of the present disclosure thus avoiding the need to apply pre-analytical sample treatment or changing the assay methodology or in a worst case of rejecting the sample.

Definitions

The term "determining" as used herein means assessing, diagnosing, deciding, identifying, evaluating, quantifying or classifying a specific analyte in a sample from the change in the optical signal of the reaction mixture of a photometric assay based on turbidimetric, nephelometric or colorimetric measurements.

The term "amount" as used herein is encompasses the absolute amount of an analyte or the relative amount and/or concentration of the analyte and/or any value and/or parameter that may correlate thereto and/or may be derived therefore.

The term "agglutination" as used herein is primarily a chemical phenomenon in which surface interaction between macromolecule leads to crosslinking and to the formation of a large complex. The formation of this large complex leads to an increase in light-scattering properties that, depending on the size of the complex, can be observed with the naked eye or monitored photometrically using turbidimetric and nephelometric detection.

The term "spectrophotometric assay", also called "photometric assay", is well known in the art. Photometric assays encompass turbidimetric and nephelometric immunoassays as well as colorimetric assays. In turbidimetric and nephelometric immunoassays the specific analyte is quantified from the change in the turbidity of the reaction mixture based on the agglutination of the specific analyte and an analyte specific binding partner, while in colorimetric assays the specific analyte is quantified with the aid of a color reagent.

The term "colorimetric assays" according to the present disclosure are routinely used in the clinical diagnostics on highly automated clinical chemistry analyzers. Due to their easy one-step procedure and their short turn-around times homogeneous colorimetric assays are ideal candidates for the application in automated analyzers. A broad test menu for the clinical chemistry analyzers are actually offered, e.g., COBAS C analyzers (Roche Diagnostics GmbH). Colorimetric assays are characterized by formation or change or the depletion of the color in the presence of the analyte to be quantified, where the formation or change or the depletion of the color is typically measured by a spectrohotometer. Since this detected color or light is typically in the visible region, you can actually see a change in the color of the assay and are therefore called colorimetric assays. Typical colorimetric tests running on lab analyzers are the clinical chemistry tests and enzyme-immuno tests (CEDIA, EMIT). The MTT assay, a redox assay using a tetrazolium dye as substrate is a further example of a colorimetric assay besides the enzymatic NAD(P)H assays. UV light is often used, since the common coenzymes NADH and NADPH absorb UV light in their reduced forms, but do not in their oxidized forms. An oxidoreductase using NADH as a substrate could therefore be assayed by following the decrease in UV absorbance at a wavelength of 340 nm as it consumes the coenzyme. Even when the enzyme reaction does not result in a change in the absorbance of light, it can still be possible to use a spectrophotometric assay for the enzyme by using a coupled assay. Here, the product of one reaction is used as the substrate of another, easily detectable reaction. An example for a coupled assay is the enzyme hexokinase, which can be assayed by coupling its production of glucose-6-phosphate to NADPH production, using glucose-6-phosphate dehydrogenase. Such assays are detected by spectrophotometry in spectrometers. The detection of these assays on the COBAS C instruments is based on a photometer with a tungsten halogen lamp as irradiation source and photodiode array (12 diodes yielding 12 wavelengths between 340 and 800 nm) as detector. The O.D. (optical density, absorbance) is directly proportional to the concentration of the colored compound. If the development of color is linked to the concentration of a substance in solution, the concentration can be measured by determining the extent of absorption of light at the appropriate wavelength. An embodiment of the present disclosure is the method wherein in colorimetric assays the specific analyte is quantified with the aid of a color reagent.

The term "color reagent" encompasses any assay reagent or a mixture of assay reagents that lead to a color change, color formation or color depletion of the assay that can be measured on the photometer with typical wavelengths ranging from 340 to 800 nm. Many colorimetric assays involve an enzyme and the corresponding substrate which lead to colored products in a one- or more-step-reaction; the color change may be induced by corresponding enzymatic co-factors like NAD/NADH rather than by the substrate itself.

There are also colorimetric assays based on the specific reaction of the analyte with a chemical reagent which leads to a colored product in a one or more step-reaction. In colorimetric immunoassays like EMIT (enzyme multiplied immunoassay technique) or CEDIA (cloned enzyme donor immunoassay) the color is typically formed by the reaction of a reporter enzyme, like ß-galactosidase or a dehydrogenase, with its corresponding substrate leading to a product with characteristic and detectable absorption properties. The reaction of the reporter enzyme with the substrate typically takes place after the immunoreaction between analyte and antibody which then triggers or inhibits the enzymatic reaction. In other colorimetric tests, like typical clinical chemistry tests for lab analyzers, the color is formed, changed or depleted by the reaction of the analyte with enzymes or any other specific chemical reagent or a combination here-off. In some cases the analyte itself acts as enzyme. Even when the enzyme reaction does not result in a change in the absorbance of light, it can still be possible to use a spectrophotometric assay for the enzyme by using a coupled assay. Here, the product of one reaction is used as the substrate of another, easily detectable reaction. An example for a coupled assay is the enzyme hexokinase, which can be assayed by coupling its production of glucose-6-phosphate to NADPH production, using glucose-6-phosphate dehydrogenase.

The term "turbidimetry and nephelometry" are methods known in the art for determining the amount of cloudiness, or turbidity, in a solution based upon measurement of the effect of this turbidity upon the transmission and scattering of light. Turbidity in a liquid is caused by the presence of finely divided suspended particles. If a beam of light is passed through a turbid sample, its intensity is reduced by scattering, and the quantity of light scattered is dependent upon the concentration, size and size distribution of the particles. The spectrophometer measures the increased turbidity (i.e., the reduction of light in the intensity transmitted light), which is due to the increasing particle size resulting from the immunoagglutination reaction. This increased turbidity is a direct measure of the immunagglutination caused by the analyte or an indirect measure of the immunagglutination inhibition caused by the analyte. In nephelometry the intensity of the scattered light is measured, while in turbidimetry, the intensity of light transmitted through the sample is measured.

Turbidimetric assays involve measurement of the intensity of the incident beam as it passes through the sample. The light beam may pass through a suspension or be absorbed, reflected, or scattered by the particles. As a consequence, the intensity of light decreases as it is transmitted through the suspension. For non-absorbing particles the decrease in light intensity due to scattering is expressed as turbidity.

Nephelometric assays refer to the measurement of the light scattered at a defined angle of θ from the incident beam when the incident beam is passed through the sample. In nephelometry the change in the intensity of the scattered light after a time is measured because the scattering species rapidly increase size. The scattered light is proportional to the initial antigen concentrations when measured in the presence of a fixed antibody-latex complex. Further explanations are described by J. A. Molina-Bolivar et al., Journal of Macromolecular Science, Part C-Polymer Review, 45:59-98, 2005.

The immunoassay method of the present disclosure works with all known agglutination tests with and without microparticles enhancement. Typically used within the present disclosure are "microparticle-enhanced light scattering agglutionation tests", which are also called "particle-enhanced turbidimetric immunoassays" (PETIA). Particle-enhanced immunoassays are routinely used in clinical diagnostics for the quantitation of serum proteins, therapeutic drugs and drugs of abuse on clinical chemistry analyzers, because they have the benefits of being quasi-homogeneous assays that do not require any separation or wash step. To enhance the optical detection between the specific analyte and an analyte specific binding partner in the reaction mixture, the analyte or the analyte specific binding partner is linked to suitable particles. Thereby, the analyte reacts and agglutinates with the particles that are coated with analyte specific binding partners. With increasing amount of analyte, the agglutination and the size of the complexes are increasing, leading further to a change of light scattering. The agglutinated particles are than determined by turbidimetric and nephelometric measurements.

The analyte comprises a mixture of particles of strong light scattering properties carrying at least one binding partner of high reactivity for the analyte and particles of weak light scattering properties carrying at least one binding partner of low reactivity for the analyte as described in European Patent No. 0 898 169. The particles of strong light scattering properties have a larger size and/or a higher refractive index than the particles of weak light scattering properties. The microparticle reagent for a microparticle enhanced light scattering immunoassay for determining the amount of an analyte, which comprises a mixture of microparticles of 30 to 600 nm in diameter, including particles of strong light scattering properties carrying at least one binding partner of high reactivity partner for the analyte and particles of weak light scattering properties carrying at least one binding partner of low reactivity for the analyte.

The material of the microparticles may be any inorganic, organic, or polymer material suitable for microparticle enhanced light scattering assays. The material of the microparticles may be any inorganic, organic, or polymer material suitable for microparticle enhanced light scattering assays. Such materials include, for example, selenium, carbon, gold; nitrides of carbon, silicium or germanium, e.g., Si3N4; oxides of iron, titanium or silicium, e.g., TiO2 or SiO2; and polymeric materials such as, for example, polystyrene, poly(vinyl chloride), epoxy resins, poly(vinylidene chloride), poly(alphanaphthyl methacrylate), poly(vinylnaphthalene), or copolymers thereof, in particular copolymers of styrene and a copolymerizable ethylenically unsaturated compound, e.g., styrene-(meth)acrylate co-polymers. Microparticles made of polymeric materials, as well as core-shell particles consisting of an inner core polymerized from styrene and an outer shell formed by copolymerization from styrene with a copolymerizable ethylenically unsaturated compound are typically suitable. The majority of particle based assays employ latex particles, with the predominant type of being polystyrene.

There are different test formats for particle-enhanced turbidimetric immunoassays (PETIA), the competitive format and the direct format. The direct format is typically applied for analytes having a large size. These analytes are polyvalent antigens with multiple epitopes, e.g., proteins and microorganisms. For the direct format the particles are coated with antibodies which agglutinate with the analyte.

Turbidimetric and nephelometric assays may also be performed in a competitive inhibition format. This format is used most often to measure small molecules, such as haptens and is usually applied in diagnostics for the drugs of abuse testing and therapeutic drug monitoring. In this format the assay reagent not only contains an analyte specific binding partner, but also a chemically modified analyte obtained by attaching it to a microsphere surface or to another carrier molecule, such as a protein (e.g., bovine serum albumin) or a soluble polymer or oligomer. In contrast to the unmodified analyte, this reagent is able to agglutinate in the presence of an analyte specific binding partner due to the multiple copies of analyte present in the molecule. The analyte in a sample is quantified from the change in the turbidity of the reaction mixture based on the aggregation of the specific analyte and an analyte specific binding partner in the presence of the modified analyte.

The antigens are linked to a cross-linking agent, e.g., polyhaptens, which compete against the antigen of the sample for the binding site of the antibody as shown in European Patent No. 0 545 350. Here a soluble polymer, a protein or a microparticle acts as carrier molecule for multiple copies of the antigen. The amount of unlabeled antigen in the test sample is measured by its ability to compete with labeled antigen in the immunoassay. The unlabeled antigen blocks the ability of the labeled antigen to bind because that binding site on the antibody is already occupied. Thus, in a competitive immunoassay, less label measured in the assay means more of the unlabeled (test sample) antigens is present.

The term "analyte" according to the present disclosure encompasses any "in vitro diagnostic compound", such as, e.g., serum proteins, therapeutic drugs and drugs of abuse. Representative analytes include, but are not limited to, antigens, haptens, antibodies, proteins, peptides, amino acids, hormones, steroids, cancer cell markers, tissue cells, viruses, vitamins, nucleic acids, pesticides, enzymes, enzyme substrates and enzyme cofactors. As used herein, an "analyte" or "specific analyte" refers to the substance whose presence and/or concentration in a sample is to be determined. The term "analyte" includes any substance for which there exists a specific reaction partner, e.g., a binding molecule or substance which specifically binds the analyte like antibodies, or a molecule which specifically reacts with the analyte, like enzymes, or for which a specific binding partner can be prepared.

The term "specific analyte" in the context of the present disclosure means that for each analyte in a sample to be measured, specific calibration curves and specific wavelengths and reaction times may be determined which are optimized for each specific analyte to quantify the concentration and which may differ from analyte to analyte.

The term "analyte specific reaction partner" as used herein is able to react with the specific analyte so as to form a reaction complex, like an antigen-antibody immunocomplex, or to form a new product, like the product resulting from an enzyme-substrate reaction. Typical analyte specific reaction partners include, but are not limited to, binding proteins, antigens, antigen fragments, antibodies, antibody fragments, nucleic acids, receptors and particle enhanced binding partners, enzymes, substrates (in cases where the analyte is an enzyme), cofactors, specific chemical reagents leading to a color change in the presence of analyte. Such reaction partners specific for a given analyte may be obtained from commercial sources or may be prepared in accordance with standard procedures known to those skilled in the art. Examples of analyte specific reaction partner pairs include, but are not limited to, hapten:antibody, cell:antibody, biotin:avidin, hormone:receptor, polypeptide:antibody, oligonucleotide:complementary DNA or RNA, enzyme-substrate, enzyme-cofactor-substrate, enzyme-mediator-substrate. For analyte specific reaction partners leading to the formation of a binding complex with the analyte, as it is the case with antibodies, the term "analyte specific binding partner" can equally be used instead of "analyte specific reaction partner".

The term "antibody" as used herein refers to immunoglobulins that are produced in response to the detection of a foreign substance, and includes intact molecules as well as functional fragments thereof, such as Fab, F (ab') 2, and Fv. Antibodies that can be used as immunological binding partners in the assay of the present disclosure include polyclonal antibodies of any species, monoclonal antibodies of any species (including chimeric antibodies and/or recombinant antibodies). Because of their capacity of being produced identically in unlimited amounts, monoclonal antibodies or fragments thereof are generally typical.

The term "antigen" as used herein is characterized by its ability to be bound at the antigen-binding site of an antibody. The region of an antigen that is recognized by an antibody, and to which the antibody binds, is referred to as an "epitope." An antigen is a substance which is capable of inducing an immune response, i.e., antibody production, when introduced into an animal or human body. A hapten is a small molecule that can elicit an immune response only when attached to a large carrier such as a protein. The carrier may be one that also does not elicit an immune response by itself. Once the body has generated antibodies to a hapten-carrier adduct, the small-molecule hapten may also be able to bind to the antibody.

The term "sample" as used herein is refers to a sample of a body fluid selected from blood, i.e., whole blood, plasma, or serum, or urine, CSF, sputum or to a sample of separated cells or to a sample from a tissue or an organ of a respective individual. Samples of body fluids can be isolated by well-known techniques. Tissue or organ samples may be isolated from any tissue or organ by, e.g., biopsy. Separated cells may be isolated from the body fluids or the tissues or organs by separating techniques such as centrifugation or cell sorting. Typically, lysates from cell-, tissue- or organ samples are isolated from those cells, tissues or organs which express or produce the peptides referred to herein.

The term "interference" as used in the present disclosure is defined as the effect of a substance present in the sample that alters the correct value of the results. A sample showing interferences as used herein refers to a sample with one or more interfering substances such as are hemoglobin, bilirubin and lipids or other interfering substances that absorb or scatter the light at wavelengths, which are commonly used for spectrophotometric tests. Further interfering substances are drugs and pharmaceuticals caused by therapies, abuses or immunoglobulines. Sometimes, in case of high concentrations of interfering substances, it is even possible to classify serum samples visually by their color.

The term "hemolysis" is defined as the release of intracellular components of erythrocytes and other blood cells into the extracellular fluid and can be caused by different mechanisms. Hemolysis in-vivo or in-vitro can cause an apparent decrease or increase of results. Cell constituents with an intracellular concentration 10 times higher than the extra-cellular concentration increase in plasma/serum during hemolysis (e.g., potassium, lactate dehydrogenase, aspartate aminotransferase). Differences of analyte concentrations between plasma and serum are also due to lysis of blood cells (essentially by platelets): Thus, neuron-specific enolase, potassium and acid phosphatase are higher in serum.

Blood cell constituents can directly or indirectly interfere in the measurement of analytes. Adenylate kinase released from erythrocytes can lead to an increase of creatine kinase and CK-MB activity especially when inhibitors of adenylate kinase in the assay mixture are inadequate. In contrast, the immunochemical quantification of CK-MB is not influenced by adenylate kinase. Pseudo-peroxidase activity of free hemoglobin is responsible for the interference in the bilirubin procedure of Jendrassik and Groof by inhibiting the diazonium color formation. Proteases released from blood cells can reduce the activity of coagulation factors while fibrin split product formation can increase.

The term "bilirubin" as used in the present disclosure occurs in plasma as a free molecule and covalently bound to albumin. In coagulation analyzers using turbidimetric principle, a bilirubin concentration exceeding 25 μmol/L leads to clinically relevant changes of the measured values of antithrombin III. At higher bilirubin concentrations interference will be significant in certain coagulation tests. The reduction of absorption of bilirubin due to oxidation under alkaline conditions is the main cause for bilirubin interference with modifications of the Jaffè method without deproteinization.

In a strongly acid environment the absorption of conjugated bilirubin shifts to the UV wavelengths and therefore causes interference in the determination of phosphate with the phosphomolybdate method through its reducing effect.

Bilirubin interferes in oxidase/peroxidase based test systems. Proportionally to its concentration bilirubin can react with $H_2O_2$ formed in the test system which causes systematically lower results in enzymatic procedures that are used for the measurement of glucose, cholesterol, triglycerides, urate and creatinine. Bilirubin competitively interferes with dyes binding to albumin.

The term "lipemia" as used in the present disclosure is defined as turbidity in serum or plasma samples which is visible to the naked eye. This is usually observed at triglyceride concentrations above 300 mg/dl (3.4 mmol/L). The most common cause of turbidity is an increased concentration of triglycerides. Lipids interfere with nearly all photometric measurement by light scattering and absorption. The apparent result can be either increased or reduced depending on the blanking procedure. At higher turbidity, no measurement may be possible due to the limits of the linearity of the method. Lipoproteins decrease the apparent concentration of the analyte by reducing the available water of sample volume, since the volume taken by lipoproteins in plasma or serum is included in the calculation of the analyte concentration. This is the cause for a lower sodium and potassium concentration in lipemic sera, when plasma or serum is measured by flame photometry and by indirect measurement using ion-sensitive electrodes, in contrast to direct potentiometry. The same observation is made after centrifugation, when the lipoproteins are not homogeneously distributed in serum/plasma samples: the concentration of an analyte dissolved in the aqueous phase is less in the upper layer than in the lower phase of the sample. The converse is true for concentration of lipids and lipid soluble constituents, including certain drugs that are taken up by lipoproteins. A constituent that is extracted by lipoproteins may not be accessible for the reagent, such as an antibody, for detection. In a similar fashion, electrophoretic and chromatographic procedures may be affected by lipoproteins present in the matrix.

The presence and amount of an interfering substance or its absence can be detected by an interference test. An example for an interfering test is the "serum indices" test which is performed at the same time as the sample is processed on a lab analyzer: By performing so called serum indices, the absorbance measurements can be calculated to provide a semi-quantitative representation of levels of icterus, hemolysis or lipemia that are present in unknown samples. Quantitative index values can be generated for the major interfering substances of hemoglobin, bilirubin, and lipids expressed as H-index (hemolysis), I-index (icterus), and L-index (lipemia). For measurement of lipemia (L), wavelengths 700/660 nm is used because this range is free from influence by hemolysis and icterus. Hemolysis (H) is measured at 600/570 nm and correction is made for absorption due to lipemia. Icterus (I) is measured at 505/480 nm and correction is made for absorption due to lipemia and hemolysis. The quality of the sample can be assessed at the same time as the sample is processed. A detailed list of interferences based on serum indices for serum and plasma for specific analytes which are determined on Roche/Hitachi Systems/Cobas Integra Systems/cobas analyzer is shown in the manual "Cobas, serum indices: reduction of clinical errors in laboratory medicine".

The term "cut-off value" as used herein, is used for a defined amount of the interfering substance. In case of serum index test the units for a defined amount of the interfering substance are the serum index values, expressed as H (for hemoglobin), L (for lipids) and I (for bilirubin) values.

The term "multiple wavelengths" as used herein refers to the wavelengths generated with a multiple wavelength photometer known in the art. Common photometers are spectrophotometers or turbidimeters for turbidimetric immunoassays and nephelometers for nephelometric immunoassays. Typically used for colorimetric assays and turbidimetric and nephelometric immunoassays is a spectrophotometer. The detection of these assays on the COBAS C instruments is based on a photometer with a tungsten halogen lamp as irradiation source, a grating for generating monochromatic light and photodiode array (12 diodes yielding 12 wavelengths between 340 and 800 nm) as detector. A photometer, e.g., the Roche COBAS C 311 analyzer has the ability to measure 12 wavelengths between 300 nm to 800±2 nm simultaneously. Typically used are the wavelengths 340, 376, 415, 450, 480, 505, 546, 570, 600, 660, 700, 800±2 nm. The method of the present disclosure is especially advantageous if used in automated analyzers, such as the COBAS C 311, having the capability of measuring multiple wavelengths simultaneously. Depending on the architecture of the chosen spectrophotometer and the available wavelengths, which may differ from device to device, one or more specific wavelengths are selected out of multiple wavelengths. The measurements are typically performed at a defined temperature, typically between 20 and 40 degree Celsius, most typically at 37° C.

The term "optical signal" as used herein describes the signal that is obtained by performing an absorbance measurement of the reaction mixture. The optical signal may be an absorbance value in case of turbidimetric and colorimetric assays or a scattered light signal for nephelometric assays. The optical signal for the specific analyte in the sample can simultaneously be measured in the reaction mixture at multiple wavelengths, typically in one run over the entire reaction time. Depending on the interfering substances, e.g., bilirubin and/or haemoglobin and/or lipids and/or other interfering substances present in the sample the amount of the specific analyte of a sample to be determined is quantified by comparison with the selected calibration curves. The choice of the calibration curve for the quantification of the specific analyte may additionally depend on the magnitude of the optical signal obtained for the specific analyte in the sample, thus taking into account, if the concentration of the specific analyte in the sample is low, or medium or high.

It is common practice to determine the concentration of an analyte by using a "calibration curve" (also commonly referred to as standard curve or working curve), which has been preliminarily drawn by plotting the interrelation between the known concentrations of the analyte in the standard samples and the analytical measured values (optical signals) such as optical densities of the standard samples. When the calibration curve has an adequate linearity over a wider range in the region of quantitative analysis, the calibration curve can be prepared with a relatively smaller number of standard samples, which are near the upper limit, lower limit and in the intermediate point in the determination range of the quantitative analysis. In practice, however, there are many calibration curves which are not linear in general. The calibration curve of turbidimetric, nephelometric or colorimetric assays, prepared from the absorbance of a specific wavelength, may have a nonlinear S-shape calibration curve where the sensitivity is deteriorated at the concentration near zero, and is saturated at a higher concentration side. The determination of the S-shape calibration requires a multipoint calibration where the use of the standard samples of the plurality of the concentrations is obliged.

When generating a calibration curve for an agglutination assay based on measurements of the turbidity of the reaction mixture, the selection of the wavelength plays, beside the reaction time, a crucial role for the slope (analytical sensitivity) of the curve and the achievable upper measuring range. For the direct assay format small wavelengths may lead to calibration curves with high slopes and high signals, whereas for the high concentration region the curves may become early a flat leading to comparable signal values for high concentrations and in consequence also to low upper detection limits. On the other hand larger wavelengths may lead to curves with small slopes but to distinguishable signal values for the high concentration region. The selection of the one wavelength and a corresponding reaction time for the signal calculation aimed at the generation of a calibration curve may therefore be a compromise between analytical sensitivity and upper measuring range. Similar situation is encountered in colorimetric assays. The selection of a wavelength near to the absorption maximum of the formed colored product ensures a high signal and high sensitivity, on the other hand the signals for high analyte concentrations may be outside of the specified optical range of the detector.

The calibration curves of the present disclosure are predetermined for the specific analyte and characterized by the used parameters for its calculation: wavelength(s), reaction time, number of calibration points, calibration mode and assay type. For the determination of a specific analyte of a sample, multiple calibration curves are generated for multiple wavelengths, each calibration curve optimized for the following cases:

interference-free samples,
hemolytic samples
icteric samples
lipemic samples
hemolytic and icteric samples
hemolytic and lipemic samples
icteric and lipemic samples
hemolytic, icteric and lipemic samples
and also for sample scenarios additionally taking the amount of the specific analyte present in the sample into account, high, low or medium.

As an example of an icteric sample with a low concentration of the specific analyte, a calibration curve is optimized for reducing the icteric interference and at the same time achieving high analytical sensitivity.

The measurement results are deposited in a data management system of the instrument platform. After preparing the measuring sample by mixing the sample with the analyte specific assay reagents, the reaction mixture is allowed to react for a given complete reaction time. The optical signal for the specific analyte of the sample to be determined in the reaction mixture is measured simultaneously at the multiple wavelengths described above for the recording of the calibration curves over the complete reaction time.

Simultaneously to the sample measurement an interference test, like the serum index evaluation, is performed for quantifying the amount of bilirubin and/or haemoglobin and/or lipids and/or other interfering substances present in the sample to be determined and the amount of each interfering substances compared to predetermined cut-off values.

Finally the calibration curve is selected in dependency of the found interferences in the interference test; and in addition to the interferences also the amount of the analyte in the sample may be taken into consideration for the selection of the calibration curve that is indicated by the magnitude of the optical signal of the sample.

In parallel to the measurement of the specific analyte to be determined in the sample, a quantitative serum index evaluation is performed on the lab analyzer for quantitation of the major interfering substances such as a hemoglobin, bilirubin, and lipids serum index. If an interfering substance is detected for the sample to be determined, a wavelength is selected for its quantitation that is outside of the absorption range of the interfering substance, but which is near to the absorption maximum of the assay mixture for the specific analyte to be determined to ensure a high signal and optimal sensitivity.

For each interference type and combinations hereof of the present disclosure a specific calibration curve is established. The calibration curves are optimized to reduce the interference for a certain concentration range of a sample showing interferences. The calibration curves can be generated under multiple conditions comprising wavelengths for measurement, reaction times, calibration mode, number of calibration points, and are predetermined for each specific analyte to be determined. All measurement results are deposited in a data management system of the instrument platform and evaluated automatically.

By using these alternative wavelengths and reaction times, which means measuring at a wavelength where the interfering substance do not absorb or absorb to a lesser extent, a reduction of interference(s) is achieved.

The term "assay type" as used herein refers to two fundamental types of photometric assays on analyzers: endpoint assays and rate assays. Measurements are taken by the photometer at specific time points. If measurements are taken after the reactions are completed, the intensity of the colored (or turbidity) product is an indicator of the sample component's concentration. These are called endpoint assays. For rate assays, the rate of the reaction is proportional to the concentration or activity of the sample component being analyzed. Measurements are taken as the reaction proceeds. There are also modifications of these two techniques possible in this instrument, as well as a combination of the two.

The term "reaction time" as used herein is in case of endpoint assays the time period between the first (or initial) and second (or final) measurement of the optical signal that is used for the calculation of a signal value hereof. The first (or initial) measurement is performed before or shortly after the final reagent is added to the reaction mixture. In case of kinetic measurements the reaction time may be the time period used for the calculation of the value expressing the absorbance change per time. The "reaction time" may be identical or shorter that the complete reaction time. The complete reaction time is the time that the reaction mixture, composed of sample and analyte specific assay reagents, is allowed to react after their mixing.

The term "calibration mode" as used herein refers to the determination of a valid relation between the measured signal [absorbance or (for rate assays) a rate of change in absorbance] and the concentration of the analyte of interest. The graphical representation of such a signal/concentration relation is the calibration curve also referred to as working curve. The analyzers use different types of mathematical models to describe this relation. These mathematical models are referred to as calibration types or calibration modes. Two basic modes of calibration exist, the linear and non-linear calibration modes. Linear calibrations are used for tests when the absorbance readings plotted against calibrator concentrations lie on a straight line. If a linear calibration is based on two calibrator measurements, it is termed linear two-point calibration. If it is based on more than two calibrators, it is termed linear multipoint calibration.

Nonlinear calibrations are used for tests whose absorbances at different concentrations form a nonlinear but reproducible plot. At least three and a maximum of six calibrators are required for calibration. A typical non-linear calibration type is the rodbard function. In addition, there are calibration types whose calibration curves are piecewise defined interpolation functions, like Spline.

The term number of calibration points as used herein is the number of calibrators also called sample standards used to generate the calibration curve. Examples for calibration curves each optimized to reduce the interference for a certain interfering substance are described below:

An embodiment of the present disclosure is calibration curve 1, which is used for a sample showing no interferences.

A further embodiment of the present disclosure is calibration curve 2, which is optimized for a sample showing hemolytic interference.

A further embodiment of the present disclosure is calibration curve 3, which is optimized for a sample showing icteric interference.

A further embodiment of the present disclosure is calibration curve 4, which is optimized for a sample showing lipemic interference.

A further embodiment of the present disclosure is calibration curve 5, which is optimized for a sample showing haemolytic and icteric or lipemic interferences.

A further embodiment of the present disclosure is calibration curve 6, which is optimized for a sample showing haemolytic and/or lipemic and/or icteric interference at low analyte concentrations. The term "calibration curve 6" as used herein is generated from the optical signals of the reaction mixture at a wavelength, optimized for achieving a satisfactory lower detection limit and at the same time optimized for reducing the interference(s). Calibration 6 curve is recorded at a wavelength that is optimized for low concentrations of the specific analyte thereby optimizing the lower detection limit and at the same time optimized for reducing the interference(s).

A further embodiment of the present disclosure is calibration curve 7, which is optimized for a sample showing hemolytic and/or lipemic and/or icteric interference at high analyte concentrations. The term "calibration curve 7" as used herein is generated from the optical signals of the reaction mixture at a wavelength, optimized for achieving a satisfactory upper detection limit and at the same time optimized for reducing the interference(s). Calibration curve 7 is recorded at a wavelength that is optimized for high concentrations of the specific analyte thereby optimizing the upper detection limit and at the same time optimized for reducing the interference(s).

A further embodiment of the present disclosure is the use of more than 2 calibration curves that may be defined over the measuring range, each optimized to reduce the interference of a sample for a certain concentration range.

Depending upon the optical signal value and the interfering substances, ideally one suitable calibration curve, as described above, are selected for the quantification of a specific analyte and the amount of the specific analyte is quantified by comparison with the selected calibration curve.

Working with multiple calibration curves instead with one calibration curve as it is done in the present disclosure may also show further benefits such as to alleviate issues related with the number and concentrations of required calibrators as well as the curve-fitting procedure for the calibration curve.

By generating multiple calibration curves under multiple conditions characterized by wavelengths for measurement, reaction times, calibration mode, number of calibration points, which were predetermined for specific analyte applications, it is now possible to measure a specific analyte of theses samplers more accurately in the comparison with standard techniques.

A calibration curve, recorded at a chosen wavelength and a chosen reaction time is selected for quantification of the specific analyte for the calculation of the analyte concentration, by the following criteria:

1. For selecting the calibration curve, a decision is made, ideally automatically on the analyzer, if the sample shows interferences and if yes, which type of interference, hemolysis, icterus and/or lipemia. This decision is made with the data obtained from the interference test or the serum index test by comparison of the obtained concentrations for each interfering substance, expressed as H-index (hemolysis), I-index (icterus), and L-index (lipemia), with predetermined cut-off values. As result the types of interferences present in the sample are obtained: the sample may be free of interferences, or be hemolytic, or be icteric, or be lipemic, or be a combination of hemolytic and/or icteric and/or lipemic. Depending on the interfering substances present in the sample, a calibration curve is selected for its quantitation: either the calibration curve for
   the interference-free sample, recorded at an optimal wavelength L(free) and optimal reaction time t(free), or
   the hemolytic sample, recorded at an optimal wavelength L(H) and optimal reaction time t(H), or
   the icteric sample, recorded at an optimal wavelength L(I) and optimal reaction time t(I), or
   the lipemic sample, recorded at an optimal wavelength L(L) and optimal reaction time t(L), or
   the hemolytic and icteric sample, recorded at an optimal wavelength L(HI) and optimal reaction time t(HI), or
   the hemolytic and lipemic sample, recorded at an optimal wavelength L(HL) and optimal reaction time t(HL), or
   the icteric and lipemic sample, recorded at an optimal wavelength L(IL) and optimal reaction time t(IL), or
   the hemolytic and icteric and lipemic sample, recorded at an optimal wavelength L(HIL) and optimal reaction time t(HIL).

2. In addition to the interferences, the calibration curve may also be selected by also taking the analyte amount present in the sample into consideration: here a comparison of the magnitude of the measured optical signal for the specific analyte of the sample with a predetermined threshold value is made in order to decide if a sample has a high or low analyte concentration. In such a case, two calibration curves would be generated to cover the measuring range for the quantitation of the analyte,
   a first calibration curve recorded at an optimal first wavelength and optimal first reaction time for the low concentrated samples, and
   a second calibration curve recorded at an optimal second wavelength and optimal second reaction time for the high concentrated samples.

Depending if the measured sample yields an optical signal or a concentration value calculated hereof that exceeds or is below the threshold value one of the two calibration curves would be used for the analyte quantitation. If necessary more concentrations levels may be considered, like the differentiation between high, medium and low concentration levels; in this case 2 predetermined threshold values are to be defined to the selection of the calibration curve.

The term "first wavelength" and first reaction time as used herein are optimized for low concentrations of the specific analyte thereby maximizing the lower detection limit. That means the first wavelength in combination with the first reaction time generates, e.g., high signals in case of the direct assay format, leading to a calibration curve which has a high analytical sensitivity.

Sensitivity, analytical sensitivity, lower detection limit (LDL), limit of blank (LOB), limit of detection (LOD) and limit of quantitation (LOQ) are terms used to describe the smallest concentration of a measurand that can be reliably measured by an analytical method. All of these terms are related but have distinct definitions (siehe Lit. din biochem rev 2008, 29, 49). For example the term "analytical sensitivity" is defined as the slope of the calibration curve. The term "lower detection limit" (LDL) as used herein is also called lower measuring range. A typical approach to estimate the LDL consists of measuring replicates, such as n=21, of a zero calibrator or blank sample, determining the mean value x and standard deviation (SD). The LDL is calculated as x+2SD or x+3SD. This method for the LDL determination is according to the method described by Kaiser (H. Kaiser, Fresenius Zeitschrift für analytische Chemie, 1965, 209, Nr. 1, pages 1-18). If the least one optical signal of a sample (out of the optical signals of the sample simultaneously measured at least at the first and second wavelengths over the complete reaction time) or the at least one signal value calculated hereof is lower than a corresponding predetermined threshold value, the concentration of the analyte is determined by comparison with the calibration curve of the first wavelength and the first reaction time for assays with increasing calibration curves.

The term "second wavelength" and second reaction time as used herein is optimized for high concentrations of the specific analyte thereby maximizing the upper detection limit. That means the second wavelength and the second reaction time generates, e.g., distinguishable signals for different analyte concentrations in the upper measuring range in case of the direct assay format leading to a calibration curve with a high upper measuring range.

The first and second wavelengths are different, ideally by at least 5 nm, or identical and the first and second reaction times may be different or identical.

The term "upper detection limit" (UDL) as used herein is also called the upper measuring range. The UDL is the highest amount of the analyte in a sample that can reliably be determined. In the present disclosure the UDL was determined by evaluating the linearity of the method and then selecting the highest concentration value within the linear range as the UDL. The method is said to be linear when the analyte recovery from a series of sample solutions (measured value) is proportional to the actual concentration of the analyte (true value) in the sample solutions (Arch Pathol Lab Med 2004, 128, pages 44-48). The form of the calibration curve, which can be parabolic or sigmoid-shaped, should not be confused with the linearity of the method that describes the relationship between the measured value and the true value. The calibration curve describes the relationship between signal and concentration.

The term "dynamic range" in the context of the present disclosure describes the magnitude of the measuring range of an assay and is here defined as ratio of upper detection limit (UDL) to lower detection limit (LDL). If not indicated otherwise we use the term measuring range as concentration values starting at the LDL and ending at the UDL. Principally other sensitivity terms may be used than the LDL, like LOD or LOQ, and also other terms describing the upper measuring range than the UDL may be used to calculate the dynamic range.

The wavelengths of the present disclosure are the so called "main wavelengths" according to the state of the art for measuring the analyte.

One embodiment of the present disclosure is that optionally a further wavelength is determined as a blank value for the correction of interferences and compensation of photometric noise, also known as bichromatic measurement (din. Chem. 1979, 25, 1482-1484). For each of the main wavelengths it is optional if a further wavelength is recorded for correction purposes by subtraction of the signal at the correction wavelength from the signal at the main wavelength.

For the each wavelength and reaction time selected for the quantification a specific analyte in a sample showing interferences one or multiple calibration curves are constructed with standard samples which are simultaneously measured.

The term "threshold value" as used herein, is used for defined absorbance values or a defined amount of the analyte of the present method, e.g., expressed as concentration value; concentration values are typically used. A threshold value is applied to the method of the disclosure when for the quantitation of an analyte one or more calibration curves are used to cover the measuring range. Typically, 2 calibration curves are used, a first calibration curve optimized for the quantitation of samples with low analyte concentrations, and a second calibration curve optimized for the quantitation of samples with high analyte concentrations. Ideally the threshold value is taken from the point where the two calibration curves change from the first calibration curve to the second calibration curve.

Figure 3:
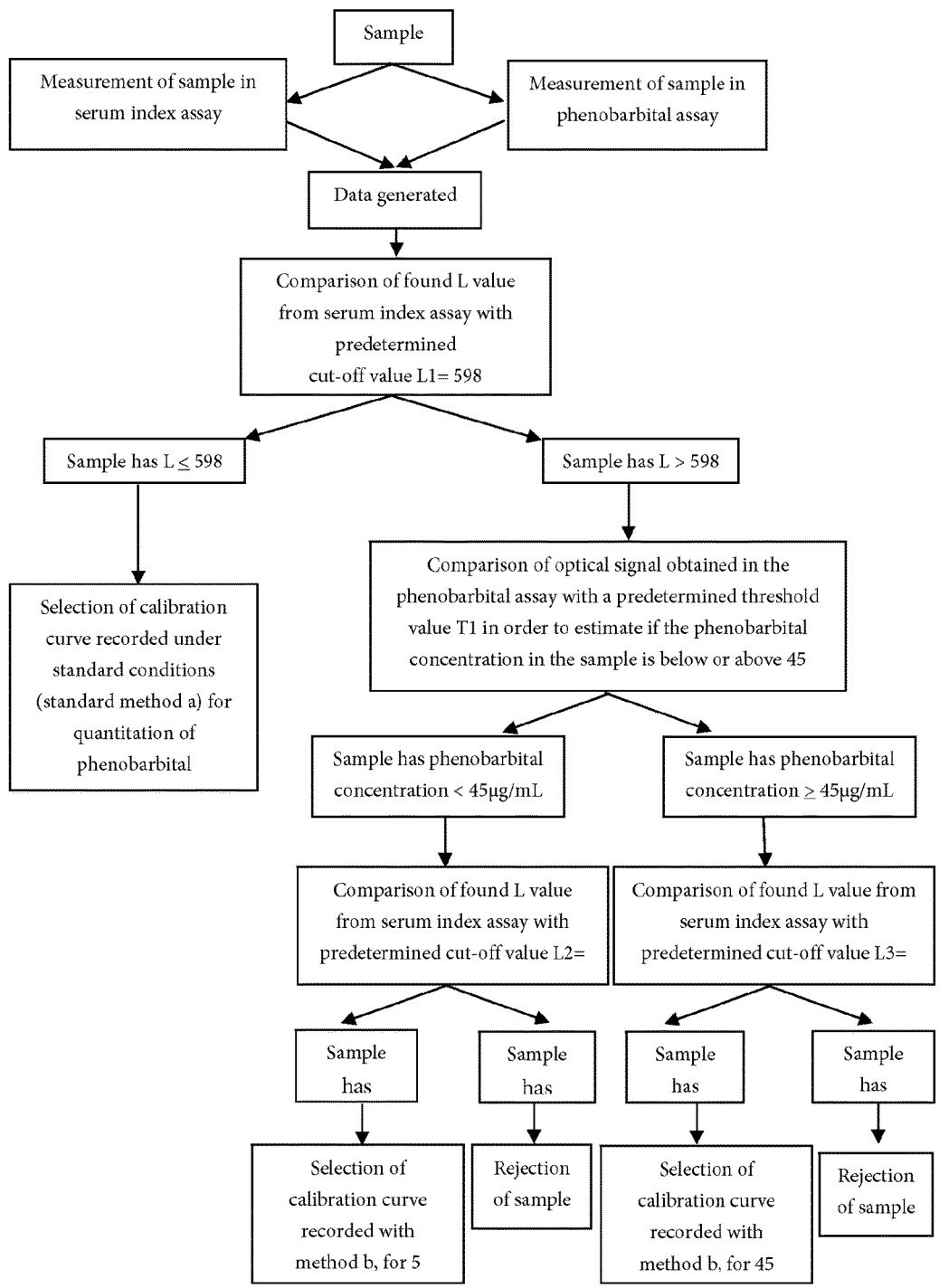
FIG. 3 shows a possible workflow for reducing lipemic interferences in the phenobarbital assay according to an embodiment of the present disclosure, as described in Example 2.

As shown in Example 2 and FIG. 3, for the phenobarbital assay two calibration curves are used for the quantitation of lipemic samples, the first calibration curve covers the concentrations from 0 to 45 μg/mL and the second calibration curve covers the concentrations from 45 to 60 μg/mL. The threshold value in this case is 45 μg/ml. It is important for an IVD assay that the threshold values are chosen at concentration which does not coincide with the clinical decision value.

For the selection of the threshold value there is usually a broad flexibility. Important is that at the selected threshold value both calibration curves fulfill the requirements related with the linearity of the method, with the precision and with the sensitivity. For example, the second calibration curve ideally should have an LDL which at least covers the concentration at the selected threshold value; and the first calibration curve ideally should show linearity of the method at least up to the said selected threshold value.

A possible procedure for the selection of the optimal measurement conditions for the calibration curves of the present disclosure comprises the following steps:

1. First, a series of data are generated at multiple wavelengths. For our Examples 1 and 2, the measurement of the absorbance values of the following samples was performed simultaneously at the 12 wavelengths available, e.g., on the COBAS C 311 analyzer over the complete reaction time:
   at least 2 to 6 standards in duplicates for the calibration,
   a blank sample (analyte concentration=0) in 21 replicates for determination of LDL,
   at least 2 samples (2 different analyte concentrations) in 21 replicates for the determination of the precision (coefficient of variation),
   dilution series covering analyte concentrations, e.g., 2-4 fold higher than the known UDL for the determination of the UDL and the linearity of the method,
   Samples containing analyte and increasing amounts of interfering substance(s) (hemoglobin, bilirubin and/or lipid) for the simulation of critical samples containing increasing amounts interfering substances.
2. The selection of the optimal wavelength and reaction time for the calibration curve for the quantitation of interference-free samples is accomplished according state-of-the-art methods.
3. The selection of the optimal wavelength and reaction time for the calibration curve for the quantitation of samples with interfering substance(s) is accomplished by selecting wavelengths that are outside or almost outside of the absorption range of the interfering substance(s), but which are still nearest to the absorption maximum of the assay mixture specific for the analyte to be determined to ensure a high signal and thus a sufficient sensitivity. The best reaction times are then selected by a trial and error method using the data generated in point 1:
   For a sample series with a fixed analyte concentration, and spiked with increasing amounts of interfering substance(s) the recovery of the theoretical analyte concentration (concentration of interference-free sample) is determined for the different conditions (optimal wavelengths as defined above, reaction times) in a trial and error procedure. An interfering substance at a given concentration is defined as tolerated (or showing no interference) when the recovery of the theoretical analyte concentration is within +/−10%. The wavelengths and reaction times yielding the best tolerance versus high concentrations of interfering substances are selected.
   For these selected wavelengths and reaction times the UDL and the LDL are calculated and the condition (wavelength and reaction time) yielding the best measuring range is selected for the calibration curve. Ideally a measuring range should be covered which is comparable with the measuring range achieved with the interference-free sample from point 2. In Example 1 this procedure was applied.
4. The selection of the optimal wavelength and reaction time for the calibration curve for the quantitation of samples with interfering substances and at the same time additionally taking the analyte amount into consideration is driven by the objective of reducing the interference(s) and at the same time obtaining a calibration with optimal measuring range. For this purpose at least two calibration curves are defined: a first calibration, recorded at a first wavelength and a first reaction time, curve for low analyte concentrations and thus covering the low end of the measuring range, and a second calibration curve, recorded at a second wavelength and a second reaction time, for high analyte concentrations and thus covering the high end of the measuring range.

A possible approach for the selection of the best conditions comprises:

the selection of optimal wavelength(s) for a given interference as described in point 3, then, for at least one sample series with low analyte concentration and one sample series with high analyte concentration, each sample series spiked with increasing amounts of interfering substance(s) the recovery of the theoretical analyte concentration (concentration of interference-free sample) is determined for the different conditions (optimal wavelengths as defined in point 3, reaction times) in a trial and error procedure. An interfering substance at a given concentration is defined as tolerated (or showing no interference) when the recovery of the theoretical analyte concentration is within +/−10%. The wavelengths and reaction times yielding the best tolerance versus high concentrations of interfering substances are selected.

For these selected wavelengths and reaction times the UDL (for the high analyte sample) and the LDL (for the low analyte sample) are calculated and the conditions (wavelength and reaction time) yielding the best measuring range are selected for the first calibration curve (low analyte sample) and second calibration curve (high analyte sample). Ideally a measuring range should be covered that is comparable with the measuring range achieved with the interference-free sample from point 2. In Example 2 this procedure was applied.

One embodiment of the present disclosure is the provision of cases for correcting calibration curves.

The term "complete reaction time" as used herein is the time period of measuring a specific analyte at a plurality of wavelengths. For the selection of the best two wavelengths aimed at the generation of the two calibration curves standards were simultaneously measured at the 12 different wavelengths available on the COBAS C instrument. Only absorbance values lying within the optical range of the detector (0.0000-3.0000 absorbance) were taken into consideration.

The typical complete reaction time of the present immunoassay time varies between 1 and 20 minutes. Typically, the complete reaction time of a multiple wavelength spectrophotometer photometer is around 10 minutes. It is an embodiment of the present disclosure that the optical signals of the specific analyte are measured during the complete reaction time. Most typically, the optical signal of the specific analyte is measured simultaneously at least at the first and at the second main wavelengths. The term "time delay" as used herein is the time period between the first and at the second main wavelength for the detection of the specific analyte.

The term "simultaneously" as used in the present disclosure may imply a time delay smaller 60× seconds, e.g., a time delay smaller 10× seconds, typically smaller 1× second, most typically smaller 1 ms, or even smaller 0.1× ms. Most typically, the term "simultaneously" means no time delay.

A further aspect of the present disclosure is a method for reducing interferences of spectrophotometric-based laboratory tests of samples showing hemolytic and/or icteric and/or lipemic interferences, wherein specific measurement conditions comprising wavelengths for measurement, assay points, calibration points, and calibration mode are additional applied to the measurement protocol without applying pre-analytical sample treatment and/or changing the assay methodology.

An embodiment is further a method according to the present disclosure, wherein one or more of the multiple calibration curves are selected depending if the sample is haemolytic and/or lipemic and/or icteric, and the amount of the specific analyte is quantified by comparison with the selected calibration curve(s).

A further aspect of the present disclosure is the use of specific measurement conditions additionally applied to the measurement protocol for reducing interferences of spectrophotometric-based laboratory tests for determining the amount of the specific analyte in a sample, which may show hemolytic and/or icteric and/or lipemic interferences comprising wavelengths for measurement, reaction times, calibration points, and calibration mode.

A further aspect of the present disclosure is an instrument platform using a commercially available spectrophotometric laboratory tests for determining the amount of the specific analyte in a sample which may show hemolytic and/or icteric and/or lipemic interferences, wherein the data management system of the instrument platform is able to process data of reaction times, calibration points, calibration mode, wavelengths, serum indices for selecting the best fitting calibration curve.

In order that the embodiments of the present disclosure may be more readily understood, reference is made to the following examples, which are intended to illustrate the invention, but not limit the scope thereof.

EXAMPLES

Example 1: Reduction of Hemolytic Interference in CRP Assay

The benefit of the method of the present disclosure for reducing the interference of hemolytic samples was assessed using Roche's commercial CRP L3 assay, a latex-enhanced turbidimetric immunoassay, and Roche's COBAS C 311 analyzer.

Instrument Cobas c 311:

Roche's COBAS C 311 analyzer (Roche Diagnostics GmbH), which has a multiple wavelength spectrophotometer as detection unit, was used for the experiments. The instrument automatically pipettes the sample and the assay reagents into reaction cells. Up to 3 different reagents, R1, R2 and R3, may be added to the sample. The instrument uses a tungsten halogen lamp as irradiation source (12 V/50 W) and measures the absorbance simultaneously at 12 different wavelengths (at 340, 376, 415, 450, 480, 505, 546, 570, 600, 660, 700 and 800±2 nm) with a photodiode array consisting of 12 photodiodes. The optical path length is 5.6 mm and the optical range of the detector is 0.0000-3.0000 absorbance. For each reaction cell, a water-blank is measured and then absorbance readings are taken 57 times in 10 minutes, here also called the complete reaction time, thus yielding a total of 57 measure points for the absorbance at each wavelength, also called photometric points or assay points. The concentration can be calculated by using at least one of these measurement points. There are two fundamental types of photometric assays on this instrument: endpoint assays and rate assays. The measurements are performed at 37 degree Celsius.

CRP L3 Assay:

Assay principle of Roche's CRP L3 test (CRPL3, Cat. No. 04956842): Human CRP agglutinates with latex particles coated with monoclonal anti-CRP antibodies; the aggregates are determined turbidimetrically.

Reagents for all Roche tests are provided in COBAS C packs. These cassettes contain from one to three specially designed reagent bottles and have barcode labels with detailed reagent and test-related. For CRP L3 tests two reagents are used in the cassette: R1 (TRIS buffer with bovine serum albumin and preservatives) and R2 (Latex particles coated with anti-CRP (mouse) in glycine buffer, immunoglobulins (mouse) and preservative). The procedure described in the package insert from the CRP L3 test was used as standard method.

Pipetting scheme: 2 μL sample and 150 μL reagent R1 were added subsequently to the reaction cell, followed by the addition of 48 μl of reagent R2, diluted with 24 μl diluent (water), and mixing of the reaction mixture.

Measurement conditions: For the measurements 570 nm was used as main wavelength and 800 nm as correction wavelength. The assay type was a two-point-end assay. A two-point-end assay is an end-point-assay which performs a sample blank. Here two absorbance readings at two different measure points are considered: the first reading is usually taken before or shortly after the final reagent is added; the second reading is taken at any time point after the final reagent was added. The absorbance value for the calibration curve and therefore for the concentration calculation is obtained by subtraction of the first reading from the second reading. For CRP L3 the first reading is at measure point 8 and means shortly after the final reagent addition, and the second reading at measure point 18, which corresponds to a reaction time of 2.0 minutes. For the generation of the calibration curve 6 standards from Roche (Cat. No. 11355279) are measured as duplicates with spline as calibration mode, which fits the ranges between the data points of the measured calibrators approximated by third degree polynomials so that a smooth calibration curve is obtained.

Procedure for Assessing the Interference:

The CRP L3 assay was run with interference-free and hemolytic samples using the standard method described in the package insert document (see below, a) and the new method (see below, b) which uses other wavelengths for the absorbance measurements compared with the standard method. The samples were measured in triplicates on the COBAS C 311. Finally the magnitude of the hemolytic interference obtained with both methods was assessed: The recovery of the measured CRP concentrations (median) was calculated for all hemoglobin containing samples and compared with the CRP value obtained with the interference-free sample. The samples are interference-free when the recovery of the initial CRP concentration value is within +/−10%; results falling within this recovery region are reportable (accurate) results.

Hemolytic serum samples: generated by adding different hemoglobin amounts to concentrations between ~154 and ~1397 mg/dL and spiking with human CRP to 5 mg/L. Interference-free serum samples: generated by spiking with human CRP to 5 mg/L.

a) Standard method:
Main wavelength: 570 nm
Sub wavelength (for correction purposes): 800 nm
Complete reaction time/reaction time: 10 min/2.0 min
6 point calibration
Calibration mode: spline
Assay type: endpoint (2-point-end)

b) New method:
Main wavelength: 600 nm
Sub wavelength (for correction purposes): 800 nm
Assay time/reaction time: 10 min/2.0 min
6 point calibration
Calibration mode: spline
Assay type: endpoint (2-point-end)

Results:

As shown in table 1, when using the standard method no interference by hemolysis is found up to an H Index of 612 (hemoglobin concentration of ~612 mg/dl). For higher H indices the recovery is outside of the +/−10% window.

As shown in table 2, when using the new method no interference by hemolysis is found up to an H Index of at least 1397 (hemoglobin concentration of ~1397 mg/dl).

This result shows an improvement of approximately factor 2.3 with respect of the hemolytic degree tolerated by the assay when using the new method. In other words, by applying the new method the hemolytic interference was reduced by a factor of 2.3. For the implementation of the new method no changes of the reagent formulation is required; only the software of the analyzer has to be adapted for a fully automatic processing of the process.

The application of the new method for the CRPL3 assay leads to some changes in the assay performance due to the variation of the wavelength and reaction time: whereas the upper detection limit (UDL) remains similar to the standard method, the lower detection limit (LDL) is slightly compromised (from 0.06 mg/L to 0.09 mg/L).

Figure 2:
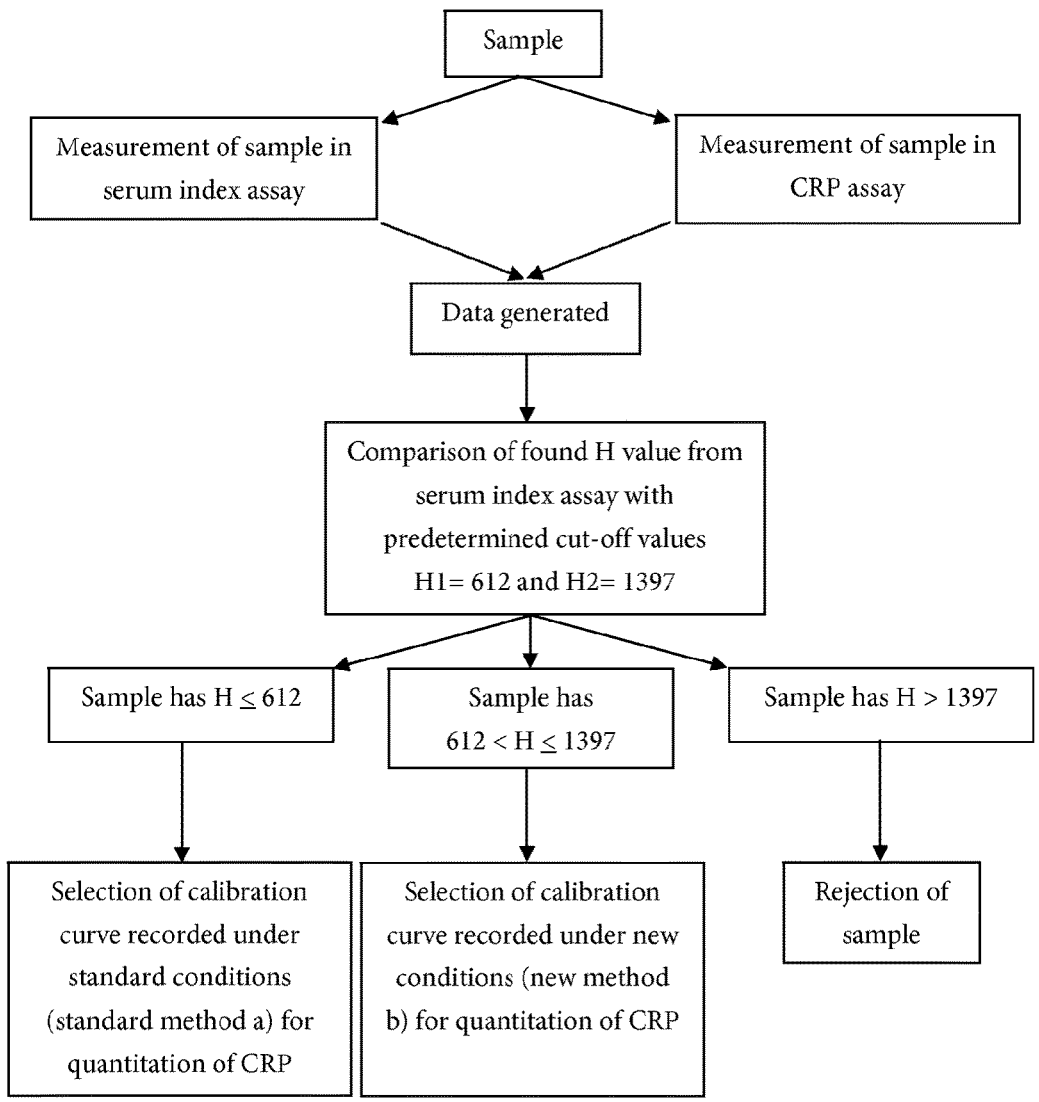
FIG. 2 shows a possible workflow for reducing hemolytic interferences in the CRP assay according to an embodiment of the present disclosure, as described in Example 1.

For this assay a possible workflow on the analyzer according to the disclosure would be (see also, FIG. 2):
Generation of calibration curves for CRP
  calibration curve recorded under standard conditions (standard method a)
  calibration curve recorded under the new conditions (new method b)
The sample is simultaneous measured in the following assays
  serum index assay, and
  the CRPL3 assay at least at the following wavelengths: 570 nm, 600 nm, 800 nm
Based on the H index value obtained in the serum index assay and its comparison with cut-off values (H=612, H=1397) the corresponding calibration curve is selected by the analyzer for the quantitation of CRP in the sample:
  H≤612: calibration curve recorded under standard conditions (standard method a)
  H>612, H≤1397: calibration curve recorded under the new conditions (new method b)
  H>1397: rejection of sample
Determination of the CRP amount in the sample by comparison of optical signal with the selected calibration curve

TABLE 1

Data for standard method:

| | | Standard method | | |
|---|---|---|---|---|
| CRP concentration in mg/L theoretical | H- Index | CRP concentration in mg/L measured | Bias vs H-Index 0 | Percent Recovery |
| 5 | 0 | 4.31 | | 100% |
| 5 | 154 | 3.99 | −7% | 93% |
| 5 | 304 | 4.00 | −7% | 93% |
| 5 | 462 | 3.89 | −10% | 90% |
| 5 | 612 | 4.01 | −7% | 93% |
| 5 | 717 | 3.83 | −11% | 89% |
| 5 | 919 | 3.80 | −12% | 88% |
| 5 | 1085 | 3.78 | −12% | 88% |
| 5 | 1240 | 3.74 | −13% | 87% |
| 5 | 1397 | 3.70 | −14% | 86% |

TABLE 2

Data for new method:

| CRP concentration in mg/L theoretical | H- Index | New method CRP concentration in mg/L measured | Bias vs H-Index 0 | Percent Recovery |
|---|---|---|---|---|
| 5 | 0 | 4.3 | | 100% |
| 5 | 154 | 4.0 | −7% | 93% |
| 5 | 304 | 4.0 | −6% | 94% |
| 5 | 462 | 4.0 | −7% | 93% |
| 5 | 612 | 4.1 | −4% | 96% |
| 5 | 717 | 4.0 | −7% | 93% |
| 5 | 919 | 4.0 | −7% | 93% |
| 5 | 1085 | 4.0 | −6% | 94% |
| 5 | 1240 | 4.0 | −6% | 94% |
| 5 | 1397 | 4.0 | −7% | 93% |

Example 2: Reduction of Lipemic Interference in Phenobarbital Assay

The benefit of the method of the present disclosure for reducing the interference of lipemic samples was assessed using Roche's commercial Phenobarbital assay, a latex-enhanced turbidimetric immunoassay (KIMS: kinetic interaction of microparticles in a solution), and Roche's COBAS C 311 analyzer.

Instrument Cobas c311:

Roche's COBAS C 311 analyzer (Roche Diagnostics GmbH), which has a multiple wavelength spectrophotometer as detection unit, was used for the experiments. The instrument automatically pipettes the sample and the assay reagents into reaction cells. Up to 3 different reagents, R1, R2 and R3, may be added to the sample. The instrument uses a tungsten halogen lamp as irradiation source (12 V/50 W) and measures the absorbance simultaneously at 12 different wavelengths (at 340, 376, 415, 450, 480, 505, 546, 570, 600, 660, 700 and 800±2 nm) with a photodiode array consisting of 12 photodiodes. The optical path length is 5.6 mm and the optical range of the detector is 0.0000-3.0000 absorbance. For each reaction cell, a water-blank is measured and then absorbance readings are taken 57 times in 10 minutes, here also called the complete reaction time, thus yielding a total of 57 measure points for the absorbance at each wavelength, also called photometric points or assay points. The concentration can be calculated by using at least one of these measurement points. There are two fundamental types of photometric assays on this instrument: endpoint assays and rate assays. The measurements are performed at 37 degree Celsius.

Phenobarbital Assay:

Assay principle of Roche's Phenobarbital test (Cat. No. 04490924): Phenobarbital antibody is covalently coupled to microparticles and the drug derivative is linked to a macromolecule. The kinetic interaction of microparticles in solutions is induced by binding of drug-conjugate to the antibody on the microparticles and is inhibited by the presence of phenobarbital in the sample. A competitive reaction takes place between the drug conjugate and phenobarbital in the serum sample for binding to the phenobarbital antibody on the microparticles. The resulting kinetic interaction of microparticles is indirectly proportional to the amount of drug present in the sample.

Reagents for all Roche tests are provided in COBAS C packs. These cassettes contain from one to three specially designed reagent bottles and have barcode labels with detailed reagent and test-related. For Phenobarbital tests two reagents are used in the cassette: R1 (Buffer with phenobarbital conjugate, preservative and stabilizer) and R2 (Latex particles coated with Phenobarbital antibody (mouse monoclonal) in buffer, preservative and stabilizer). The procedure described in the package insert from the Phenobarbital test was used as standard method.

Pipetting scheme: 2 µL sample and 93 µL reagent R1 were added subsequently to the reaction cell, followed by the addition of 93 µl of the reagent R2 and mixing of the reaction mixture.

Measurement conditions: For the measurements 600 nm was used as main wavelength and 800 nm as correction wavelength. The assay type was a two-point-end assay. A two-point-end assay is an end-point-assay which performs a sample blank. Here two absorbance readings at two different measure points are considered: the first reading is usually taken before or shortly after the final reagent is added; the second reading is taken at any time point after the final reagent was added. The absorbance value for the calibration curve and therefore for the concentration calculation is obtained by subtraction of the first reading from the second reading. For phenobarbital the first reading is at measure point 10 and means shortly after the final reagent addition, and the second reading at measure point 49, which corresponds to a reaction time of 6.5 minutes. For the generation of the calibration curve 6 standards from Roche (Cat. No. 03375790) are measured as duplicates with RCM (Rodbard function) as calibration mode.

Procedure for Assessing the Interference:

The Phenobarbital assay was run with interference-free and lipemic samples using the standard method described in the package insert document (see below, a) and the new method (see below, b), which uses other wavelengths for the absorbance measurements compared with the standard method. The samples were measured in triplicates on the COBAS C 311. Finally the magnitude of the lipemic interference obtained with both methods was assessed: The recovery of the measured phenobarbital concentrations (median) was calculated for all lipid containing samples and compared with the phenobarbital value obtained with the interference-free sample. The samples are interference-free when the recovery of the initial phenobarbital concentration value is within +/−10%; results falling within this recovery region are reportable (accurate) results.

Lipemic serum samples: generated by adding different intralipid amounts to concentrations between ~6 and ~1903 mg/dL and spiking with phenobarbital to 5 and 45 µg/mL respectively.

Interference-free serum samples: generated by spiking with phenobarbital to 5 and 45 µg/mL respectively.

a) Standard method:
Main wavelength: 600 nm
Sub wavelength (for correction purposes): 800 nm
Complete reaction time/reaction time: 10 min/6.5 min
6 point calibration
Calibration mode: RCM (Rodbard)
Assay type: endpoint (2-point-end)
b) New method:
For phenobarbital concentration 5 µg/mL:
Main wavelength: 505 nm
Sub wavelength (for correction purposes): 800 nm
Complete reaction time/reaction time: 10 min/6.5 min
6 point calibration
Calibration mode: RCM (Rodbard)
Assay type: endpoint (2-point-end)
For phenobarbital concentration 45 µg/mL:

Main wavelength: 450 nm
Sub wavelength (for correction purposes): 800 nm
Complete reaction time/reaction time: 10 min/3.6 min
6 point calibration
Calibration mode: RCM (Rodbard)
Assay type: endpoint (2-point-end)
Results:

As shown in Table 3 for a phenobarbital concentration of 5 μg/mL, when using the standard method no interference by lipemia is found up to an L Index of 598 (intralipid concentration of ~598 mg/dl). For higher L indices the recovery is outside of the +/−10% window.

As shown in Table 4 for a phenobarbital concentration of 5 μg/mL, when using the new method no interference by lipemia is found up to an L Index of 902 (intralipid concentration of ~902 mg/dl).

As shown in Table 5 for a phenobarbital concentration of 45 μg/mL, when using the standard method no interference by lipemia is found up to an L Index of 802 (intralipid concentration of ~802 mg/dl). For higher L indices the recovery is outside of the +/−10% window.

As shown in Table 6 for a phenobarbital concentration of 45 μg/mL, when using the new method no interference by lipemia is found up to an L Index of 1262 (intralipd concentration of ~1262 mg/dl).

These results shows an improvement of approximately factor 1.5 with respect of the lipemic degree tolerated by the assay when using the new method (see table 7). With other words, by applying the new method the lipemic interference was reduced by a factor of 1.5. For the implementation of the new method no changes of the reagent formulation is required; only the software of the analyzer has to be adapted for a fully automatic processing of the process.

The application of the new method for the Phenobarbital assay leads to no changes in the assay performance due to the variation of the wavelength and reaction time: LDL and UDL remain similar to the standard method.

Therefore, for this assay a possible workflow on the analyzer according to the disclosure would be (see also, FIG. 3):

1. Generation of calibration curves for Phenobarbital
    calibration curve recorded under standard conditions (standard method a)
    two calibration curves recorded under the new conditions (new method b)
2. The sample is simultaneous measured in the following assays
    serum index assay and
    the phenobarbital assay at least at the following wavelengths: 450 nm, 505 nm, 600 nm, 800 nm
3. Based on the L index value obtained in the serum index assay and its comparison with cut-off values (L1=598, L2=902, L3=1262), and based on the rough estimation of the phenobarbital concentration by comparison of the optical signal of the sample obtained in the phenobarbital assay with a predetermined threshold value T1 (T1 may be the optical signal in the calibration curve measured with the standard method corresponding to a phenobarbital concentration of 45 μg/mL), the corresponding calibration curve is selected by the analyzer for the quantitation of phenobarbital in the sample:
    L≤598→calibration curve recorded under standard conditions (standard method a), independently from phenobarbital concentration in
    L>598→selection of calibration curve based on found L-index and also based on rough phenobarbital concentration in the sample by comparison of measured optical signal from the sample in the phenobarbital assay with a corresponding threshold value:
    if L>598 and L≤902 and
    if measured optical signal indicates a phenobarbital concentration<45 μg/mL:
    →calibration curve recorded under the new conditions (new method b, conditions for 5 μg/mL phenobarbital)
    if L>598 and L>902 and
    if measured optical signal indicates a phenobarbital concentration<45 μg/mL:
    →rejection of sample
    if L>598 and L≤1262 and
    if measured optical signal indicates a phenobarbital concentration≥45 μg/mL:
    →calibration curve recorded under the new conditions (new method b, conditions for 45 μg/mL phenobarbital)
    if L>598 and L>1262 and
    measured optical signal indicates a phenobarbital concentration≥45 μg/mL:
    →rejection of sample
4. Determination of the phenobarbital amount in the sample by comparison of optical signal with the selected calibration curve.

TABLE 3

5 μg/ml phenobarbital: Data for standard method (600-800 nm, 6.5 min)

| | | Standard | | |
|---|---|---|---|---|
| Phenobarbital concentration in μg/mL theoretical | L- Index | Phenobarbital concentration in μg/mL measured | Bias vs L-Index 0 | Percent Recovery |
| 5 | 7 | 4.6 | | 100% |
| 5 | 145 | 4.7 | 0.1 | 102% |
| 5 | 292 | 4.6 | 0.0 | 99% |
| 5 | 453 | 4.4 | −0.3 | 94% |
| 5 | 598 | 4.2 | −0.4 | 91% |
| 5 | 736 | 3.9 | −0.7 | 85% |
| 5 | 902 | 3.6 | −1.0 | 78% |
| 5 | 1056 | 3.3 | −1.3 | 71% |
| 5 | 1289 | 3.0 | −1.6 | 66% |
| 5 | 1349 | 2.8 | −1.8 | 61% |
| 5 | 1485 | 2.4 | −2.2 | 51% |

TABLE 4

5 μg/ml phenobarbital: Data for new method (505-800 nm, 6.5 min)

| | | New method | | |
|---|---|---|---|---|
| Phenobarbital concentration in μg/mL theoretical | L- Index | Phenobarbital concentration in μg/mL measured | Bias vs L-Index 0 | Percent Recovery |
| 5 | 7 | 4.6 | | 100% |
| 5 | 145 | 4.8 | 0.2 | 104% |
| 5 | 292 | 4.7 | 0.1 | 102% |
| 5 | 453 | 4.6 | 0.0 | 99% |
| 5 | 598 | 4.6 | −0.1 | 99% |
| 5 | 736 | 4.4 | −0.2 | 95% |
| 5 | 902 | 4.2 | −0.4 | 92% |
| 5 | 1056 | 4.1 | −0.5 | 89% |
| 5 | 1289 | 4.0 | −0.6 | 87% |
| 5 | 1349 | 4.0 | −0.6 | 86% |

TABLE 5

45 µg/ml phenobarbital: Data for standard method (600-800 nm, 6.5 min)

| | | Standard method | | |
|---|---|---|---|---|
| Phenobarbital concentration in µg/mL theoretical | L- Index | Phenobarbital concentration in µg/mL measured | Bias vs L-Index 0 | Percent Recovery |
| 45 | 6 | 39.6 | | 100% |
| 45 | 154 | 39.1 | −1% | 99% |
| 45 | 313 | 38.8 | −2% | 98% |
| 45 | 472 | 38.3 | −3% | 97% |
| 45 | 656 | 37.7 | −5% | 95% |
| 45 | 802 | 37.0 | −7% | 93% |
| 45 | 967 | 35.3 | −11% | 89% |
| 45 | 1262 | 33.9 | −14% | 86% |
| 45 | 1419 | 30.6 | −23% | 77% |
| 45 | 1526 | 31.4 | −21% | 79% |
| 45 | 1670 | 31.0 | −22% | 78% |
| 45 | 1780 | 29.2 | −26% | 74% |
| 45 | 1903 | 28.5 | −28% | 72% |

TABLE 6

45 µg/ml phenobarbital: Data for new method (450-800 nm, 3.6 min)

| | | New method | | |
|---|---|---|---|---|
| Phenobarbital concentration in µg/mL theoretical | L- Index | Phenobarbital concentration in µg/mL measured | Bias vs L-Index 0 | Percent Recovery |
| 45 | 6 | 40.2 | | 100% |
| 45 | 154 | 40.2 | −0.1% | 100% |
| 45 | 313 | 39.6 | −2% | 98% |
| 45 | 472 | 39.6 | −2% | 98% |
| 45 | 656 | 39.2 | −2% | 98% |
| 45 | 802 | 38.5 | −4% | 96% |
| 45 | 967 | 37.4 | −7% | 93% |
| 45 | 1262 | 36.8 | −9% | 91% |
| 45 | 1419 | 34.3 | −15% | 85% |
| 45 | 1526 | 35.2 | −12% | 88% |
| 45 | 1670 | 34.2 | −15% | 85% |
| 45 | 1780 | 33.4 | −17% | 83% |
| 45 | 1903 | 33.4 | −17% | 83% |

TABLE 7

Comparison of standard and new method for phenobarbital aimed at reduction of lipemia interference

| Interference assessed at following analyte concentrations | Tolerated amounts of interfering substance§ with standard method* | Tolerated amounts of interfering substance§ with new method* | Improvement factor |
|---|---|---|---|
| | 600 nm-800 nm, 6.5 min: | 505 nm-800 nm, 6.5 min: | |
| 5 µg/mL phenobarbital | L index ≤ 598 | L index < 902 | 1.5 |
| | | 450 nm-800 nm, 3.6 min: | |
| 45 µg/mL phenobarbital | L index ≤ 802 | L index < 1262 | 1.5 |

*Methods are described by indicating the used main wavelength, correction wavelength, reaction time
§L index 1 is approximately 1 mg/dL lipid It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present invention.

It is also noted that the terms "substantially" and "about" may be utilized herein to represent the inherent degree of uncertainty that may be attributed to any quantitative comparison, value measurement, or other representation. These terms are also utilized herein to represent the degree by which a quantitative representation may vary from a stated reference without resulting in a change in the basic function of the subject matter at hand.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modifications and variations come within the scope of the appended claims and their equivalents.

What is claimed is:

1. A method for reducing interference caused by presence of one or more interfering substances (IS) in an automated photometric platform for measuring an amount of a specific analyte in a biological sample, the method comprising:
    a) generating a data base of calibration curves, the data base comprising at least one calibration curve for at least the following samples:
        a sample comprising specific analyte free of IS;
        a sample comprising specific analyte and IS, for each IS;
        a sample comprising specific analyte and a combination of IS, for each combination of IS; and, optionally, the samples in replicate for more than one concentration of specific analyte;
    b) depositing the database into a data management system of the automated platform;
    c) adding a measuring sample to a photometric assay of the platform without pre-treating the measuring sample to remove or neutralize IS, and without initiating a blanking procedure;
    d) photometrically generating a series of optical signals at multiple wavelengths selected to measure the specific analyte in the measuring sample across a time frame;
    e) simultaneously generating a series of optical signals at the multiple wavelengths to quantify each of the one or more IS across the time frame and quantifying an amount of each of the one or more IS;

f) selecting a calibration curve from the data base in accordance with the quantification result of step d); and g) measuring the amount of specific analyte in the measuring sample according to the calibration curve selected.

2. The method according to claim 1, wherein the quantification result of step (e) shows no interferences and step (f) comprises selecting a calibration curve 1 recorded at a wavelength 1 for a sample showing no interferences.

3. The method according to claim 1, wherein the quantification result of step (e) shows hemolytic interference and step (f) comprises selecting a calibration curve 2 recorded at a wavelength 2, which is optimized for a sample showing hemolytic interference.

4. The method according to claim 1, wherein the quantification result of step (e) shows icteric interference and step (f) comprises selecting a calibration curve 3 recorded at a wavelength 3, which is optimized for a sample showing icteric interference.

5. The method according to claim 1, wherein the quantification result of step (e) shows lipemic interference and step (f) comprises selecting a calibration curve 4 recorded at a wavelength 4, which is optimized for a sample showing lipemic interference.

6. The method according to claim 1, wherein the quantification result of step (e) shows a combination of two or more of hemolytic, icteric and lipemic interferences and step (f) comprises selecting a calibration curve 5 recorded at a wavelength 5, which is optimized for a sample showing the combination of interferences.

7. The method according to claim 1, wherein the data base comprises calibration curves for samples in replicate for at least a low concentration and a high concentration of specific analyte.

8. The method according to claim 7, wherein the quantification result of step (e) shows hemolytic interference and step (f) comprises selecting a calibration curve 6 recorded at a wavelength 6, which is optimized for a sample showing hemolytic interference at low analyte concentrations.

9. The method according to claim 8, wherein the quantification result of step (e) shows hemolytic interference and step (f) comprises selecting a calibration curve 7 recorded at a wavelength 7, which is optimized for a sample showing hemolytic interference at high analyte concentrations.

10. The method according to claim 1, wherein the interfering substances derive from one or more of hemolytic (H), icteric (I) and lipemic (L) interferences and the data base comprises calibration curves for:

sample comprising specific analyte free of H, I and L;
sample comprising specific analyte and H;
sample comprising specific analyte and I;
sample comprising specific analyte and L;
sample comprising specific analyte, H and I;
sample comprising specific analyte, H and L;
sample comprising specific analyte, I and L;
sample comprising specific analyte, H, I and L; and
each sample in replicate for more than one concentration of specific analyte.

11. The method according to claim 1, wherein the photometric assay comprises a colorimetric assay and the optical signal comprises light absorbance.

12. The method according to claim 1, wherein the photometric assay comprises a turbidimetric assay and the optical signal comprises intensity of transmitted light.

13. The method according to claim 1, wherein the photometric assay comprises a nephelometric assay and the optical signal comprises intensity of scattered light.

* * * * *